US006696287B2

(12) United States Patent
Paoletti et al.

(10) Patent No.: US 6,696,287 B2
(45) Date of Patent: Feb. 24, 2004

(54) SYSTEM FOR CO-CULTURING BACTERIA AND EUKARYOTIC CELLS

(75) Inventors: Lawrence C. Paoletti, Wilmington, MA (US); Gennady Malin, Newton, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 26 days.

(21) Appl. No.: 10/100,177

(22) Filed: Mar. 19, 2002

(65) Prior Publication Data

US 2002/0146808 A1 Oct. 10, 2002

Related U.S. Application Data

(60) Provisional application No. 60/279,436, filed on Mar. 29, 2001.

(51) Int. Cl.[7] .......................... C12M 1/00; C12M 3/00; C12Q 1/00; C12N 5/00; C12N 1/20
(52) U.S. Cl. ................... 435/294.1; 435/289.1; 435/297.5; 435/4; 435/29; 435/325; 435/243; 435/253.4; 435/283.1; 435/287.1; 435/288.5; 435/252.1; 435/347
(58) Field of Search ................... 435/4–29, 325, 435/243, 283.1, 287.1, 288.5, 252.1, 289.1–305.4, 253.4, 347

(56) References Cited

U.S. PATENT DOCUMENTS

| | | |
|---|---|---|
| 5,310,654 A | 5/1994 | Isberg et al. |
| 5,565,353 A | 10/1996 | Klebe et al. |
| 5,660,977 A | 8/1997 | Flores-Cotera et al. |
| 5,693,537 A | 12/1997 | Wilson et al. |

OTHER PUBLICATIONS

Malin, et al., "B–182. Growth Rate Influences Invasion of Respiratory Epithelial Cells by Group B Streptococcus: Use of Dynamic In Vitro Attachment and Invasion System (DIVAS), a New Method to Study Bacterial Pathogenesis," *Abstracts of the General Meeting of the American Society for Microbiology* 101:82 (2001).

Hulten, et al., "New Pharmacokinetic in Vitro Model for Studies of Antibiotic Activity against Intracellular Microorganisms," *Antimicrob. Agents Chemother.* 40:2727–2731 (1996).

Paoletti, et al., "Cell Growth Rate Regulates Expression of Group B Streptococcus Type III Capsular Polysaccharide," *Infect. Immun.* 64:1220–1226 (1996).

Ross, et al., "Regulation of Cell Component Production by Growth Rate in the Group B Streptococcus," *J. Bacteriol.* 181:5389–5394 (1999).

Rubens, et al., "Transposon Mutagenesis of Type III Group B Streptococcus: Correlation of Capsule Expression with Virulence," *Proc. Natl. Acad. Sci. USA* 84:7208–7212 (1987).

Rubens, et al., "Respiratory Epithelial Cell Invasion by Group B Streptococci," *Infect. Immun.* 60:5157–5163 (1992).

Tamura, et al., "Adherence of Group B Streptococci to Cultured Epithelial Cells: Roles of Environmental Factors and Bacterial Surface Components," *Infect. Immun.* 62:2450–2458 (1994).

*Primary Examiner*—Gerald G. Leffers, Jr.
(74) *Attorney, Agent, or Firm*—Michael A. Sanzo; Fitch, Even, Tabin & Flannery

(57) ABSTRACT

The present invention is directed to an apparatus that can be used for co-culturing bacteria and eukaryotic cells. The apparatus allows the bacteria to be grown under steady state conditions and then perfused over the eukaryotic cells. The invention also includes a variety of methods for studying the attachment and invasion of host eukaryotic cells by bacteria.

21 Claims, 2 Drawing Sheets

SYSTEM FOR CO-CULTURING BACTERIA AND EUKARYOTIC CELLS

CROSS REFERENCE TO RELATED APPLICATIONS

The present application claims the benefit of U.S. provisional application No. 60/279,436, filed on Mar. 29, 2001.

STATEMENT OF GOVERNMENT FUNDING

The United States Government has a paid-up license in this invention and the right in limited circumstances to require the patent owner to license others in reasonable terms as provided for by the terms of NIH Grant No. NO 1-AI-75326 awarded by the Department of Health and Human Services.

FIELD OF THE INVENTION

The present invention is directed to a system for co-culturing bacteria and eukaryotic cells. The apparatus allows bacteria that are in a controlled state of growth to be perfused over immobilized eukaryotic cells. In addition, the invention includes a variety of methods for studying the attachment and invasion of host cells by bacteria.

BACKGROUND OF THE INVENTION

At present, most protocols for studying the interaction between bacteria and host tissue involve growing the bacteria in batch culture, placing them onto a monolayer of eukaryotic cells, and then treating the monolayer to study either attachment or invasion. However, growth rate cannot be controlled using batch culture methods. Since expression of bacterial cell surface proteins is essential for their invasion of host cells, and since it is known that such expression can be altered by growth rate, this is a serious drawback (see Paoletti, et al., *Infect. Immun.* 64:1220–1226 (1996); Ross, et al., *J Bacteriol.* 181:5389–5394 (1999)).

Although methods for growing bacteria under defined steady state conditions are known and systems for perfusing cultured eukaryotic cells with media have been disclosed (see e.g., U.S. Pat. No. 5,565,353; U.S. Pat. No. 5,693,537; Hulten et al., *Agents Chemother.* 40:2727–2731 (1996)), these have not been combined into an effective system for studying the interactions between invasive bacteria and their hosts. The development of such a system would have a number of important applications. First, the ability to separate invasive bacteria from their non-invasive counterparts should aid researchers in determining the mechanisms involved in the invasion process and may lead to the development of new therapeutic strategies for treating bacterial diseases. The technology could also be used to screen for therapeutic agents that act by preventing bacterial attachment and invasion. In addition, defining the growth conditions which increase bacterial invasiveness would allow cells to be grown that are especially well suited to the development of antibodies for diagnostic or therapeutic purposes.

SUMMARY OF THE INVENTION

The present invention is based upon the discovery that growth conditions affect the ability of bacteria to invade host cells. This has led the inventors to develop a system for combining previously unrelated methods for growing bacterial and eukaryotic cells. The key element of the system is that bacteria are grown at a defined rate under steady state conditions and used to perfuse eukaryotic cells that are attached to a solid support, thus preserving a defined bacterial state at all times during their interaction with eukaryotic cells. The apparatus and methods developed should be useful to researchers studying bacterial diseases and should aid in the development of new therapeutic and diagnostic procedures.

In its first aspect, the invention is directed to an apparatus in which eukaryotic and bacterial cells are co-cultured under different conditions. The apparatus has a fermentor in which bacteria are grown at a fixed rate under steady state conditions. The fermentor must have at least one inlet port for receiving materials needed to maintain bacterial growth (e.g., growth medium). By altering the availability of one or more nutrients, e.g., glucose, the rate at which the bacteria grow can be controlled. Thus, the inlet port will typically be connected via tubing to a reservoir of nutrient medium and means for actively delivering this medium to the port will be present. The fermentor may also include a second inlet port for receiving materials and which may be connected to a second reservoir. For example, the second inlet port might be used to deliver a solution to help control the pH at which cells are grown. In addition, the fermentor should have at least one outlet port through which fluid from inside the fermentor, comprised of growth medium and bacteria, can pass. It should also have means for mixing the fluid it contains, e.g., a rotating paddle mixer.

The apparatus includes a culture vessel containing eukaryotic cells attached to a solid support. This vessel may take the form of a tissue culture flask, dish, or multiwell plate in which cells are attached either directly to the walls of the vessel or to a matrix used to coat the walls. It may also take the form of a column that has been packed with a porous support (e.g., beads or membranes) on which cells have been grown or even roller bottles adapted to be used with the system. The culture vessel must have at least one inlet port connected, usually by polymeric tubing, to the outlet port of the fermentor. Means for moving fluid from the fermentor's outlet port to the inlet port of the culture vessel must also be available to allow the eukaryotic cells to be perfused with bacteria from the fermentor. Any type of pump compatible with biological systems, e.g., a peristaltic pump, can be used for this purpose. In addition, the culture vessel must have at least one outlet port for removing fluid. Since the eukaryotic cells are immobilized by being attached to a solid support, they remain within the culture vessel as fluid is removed. Although such removal may take place through the outlet port passively in response to fluid being pumped in, it is preferred that means for actively extracting fluid, e.g., a pump, be present.

In a preferred embodiment, the fermentor of the apparatus described above contains a second outlet port for removing fluid which, unlike the first outlet port, is not connected to the culture vessel. The second outlet is used to maintain a constant volume and allows the rate at which nutrient material enters into the fermentor to be altered without the need for changing the rate at which eukaryotic cells are perfused.

In another aspect, the invention is directed to a method for assaying bacteria for their ability to attach to and invade eukaryotic cells. This is accomplished by growing the bacteria in a continuous culture fermentor under steady state conditions and simultaneously perfusing the growing bacteria over eukaryotic cells that are attached to a solid support. The invasiveness of the bacteria can then be determined by lysing the eukaryotic cells and counting the number of colony forming units of bacteria. This can be done either directly or, the culture flask can be removed from the apparatus, further incubated if desired, and then inspected microscopically. Other means for determining the extent to which bacteria have attached to and invaded eukaryotic cells are also compatible with the invention. The apparatus described above is particularly well suited for this assay although alternative systems can be employed if desired.

The ability to separate bacteria that attach to eukaryotic cells from those that do not is of interest to researchers studying bacterial diseases. The apparatus described above lends itself to a method for accomplishing such a separation. Again, bacteria are grown in a continuous culture fermentor under steady state conditions and allowed to perfuse eukaryotic cells attached to a solid support. When the perfusate is removed from the cells, unattached bacteria are eliminated and those attached to the eukaryotic cells remain behind. After washing, e.g., with bacteria-free medium, the attached bacteria can either be studied directly or grown in suspension. In some instances, it may also be desirable to collect the perfusate from the culture vessel in order to obtain bacteria that do not attach to eukaryotic cells. This could be useful for scientists wanting to compare the characteristics of invasive bacteria with their non-invasive counterparts.

The invention also includes a method of assaying a test compound for its ability to block the invasion of eukaryotic cells by bacteria, or to clear invaded bacteria from infected cells. Similar to the methods described above, bacteria are grown in a continuous culture fermentor under steady state conditions and then used to perfuse eukaryotic cells that are attached to a solid support. The number of bacteria that invade the eukaryotic cells is determined and then this entire process is repeated in the presence of the test compound. A reduction in the number of eukaryotic cells invaded would be an indication that the test compound acts as a blocking agent or is effective as an intracellular antibacterial agent, and has potential use as a therapeutic.

In another aspect, the basic procedures described above can be adapted to a method of selecting a growth rate at which the invasiveness of bacteria for eukaryotic cells is increased. Cells of increased invasiveness are of interest to scientists studying bacterial diseases as well as to those trying to develop antibodies that can be used for either therapeutic or diagnostic purposes. The method is performed by growing bacteria under steady state conditions at a first growth rate, perfusing these bacteria over eukaryotic cells as described above, and then determining the extent to which the cells are invaded. This process is then repeated at a second growth rate to determine which conditions lead to the most invasion. By performing the process several times, optimized conditions for growing bacteria can be determined.

BRIEF DESCRIPTION OF THE FIGURES

FIG. 1 depicts a preferred embodiment of the present invention. The reference letters used in the figure refer to the following structures: A, reservoir containing growth medium; B, pump connecting reservoir A with inlet port of fermentor; C, second reservoir containing a basic solution for regulating the pH of the fluid inside the fermentor; D, pump connecting second reservoir with second inlet port of fermentor; E, fermentor for growing bacteria; F, outlet port of fermentor for maintaining a constant fluid level; G, pump connecting outlet port of fermentor with waste container; H, inlet port for fermentor connected to reservoir C by pump D; I, inlet port for fermentor connected to reservoir A by pump B; J, second outlet port of fermentor connected to inlet port N of flask M by pump K; K, pump connecting outlet port of fermentor to inlet port of flask; L, stir motor for fermentor; M, tissue culture flask with inlet and outlet ports; N, inlet port of tissue culture flask; O, outlet port of tissue culture flask; P, pump connecting outlet port O of flask to waste; Q, waste receptacle for material received from outlet port of flask; and R, receptacle for waste received from fermentor.

FIG. 2 shows plastic tissue culture flasks that have been modified to have an inlet and outlet port. The inlet port may be formed by puncturing the flask with a hot sterile 21 gauge needle. The outlet port may be formed in a similar manner using either a 16 or 18 gauge needle and, in the figure, is attached to a female luer connector.

DETAILED DESCRIPTION OF THE INVENTION

Figure 1:
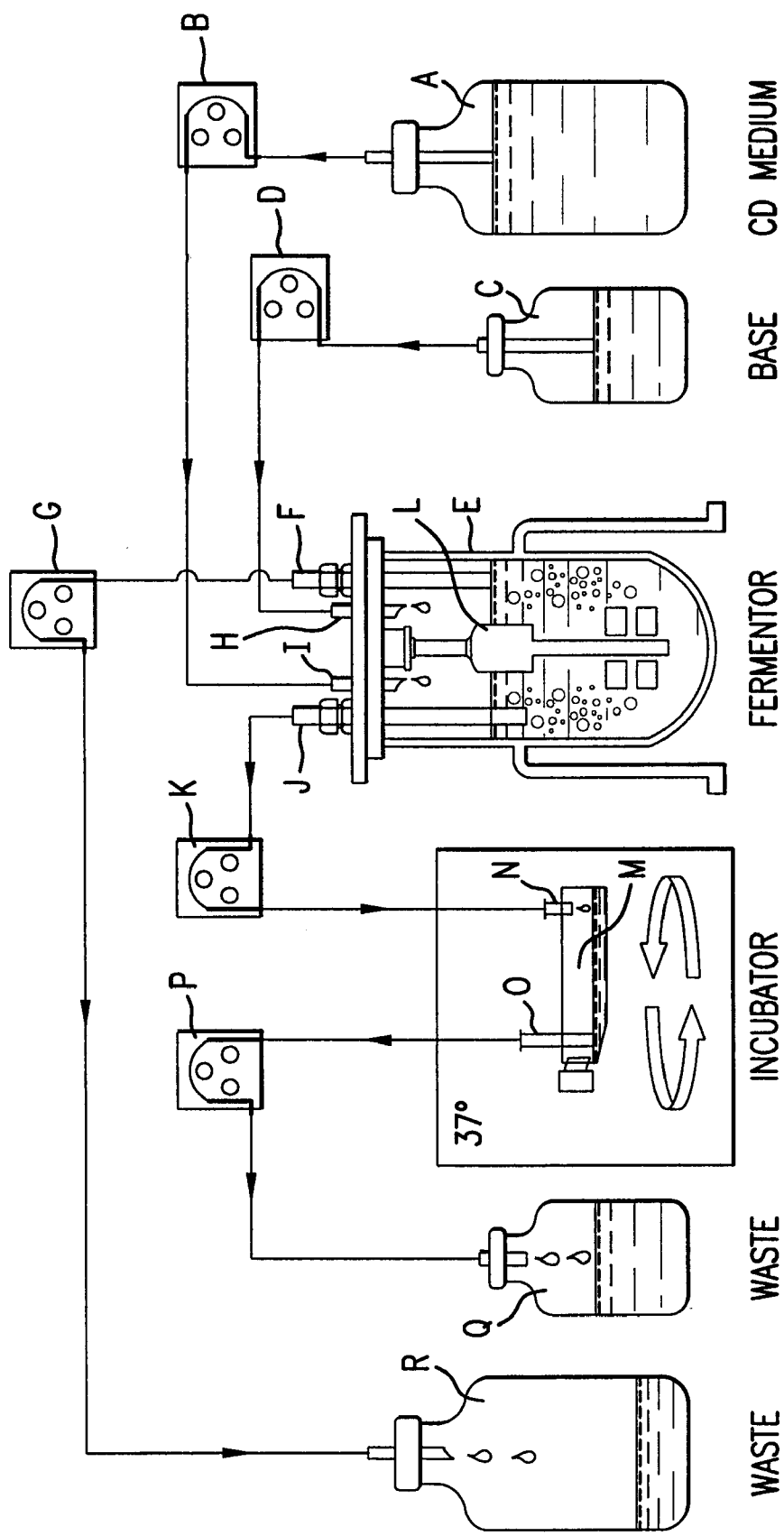
FIG. 1.

The present invention is directed to an apparatus for growing bacterial cells under steady state conditions and then directly exposing eukaryotic cells to these bacteria. The apparatus is made up of standard components that are readily available from commercial sources. One preferred embodiment is illustrated in FIG. 1. This shows a fermentor (E) that can be used for continuously culturing bacteria under steady state conditions. The fermentor has an inlet port (I) that is used to introduce nutrient-containing medium to growing bacteria. By altering the availability of nutrients, the growth of the bacteria can be maintained at a defined rate. The figure shows a reservoir (A) that is attached by pump (B) to the fermentor's inlet port. Typically, this connection and the others shown in the figure will be made using flexible polymeric tubing. The figure also shows the fermentor as having a second, optional, inlet port (H) connected by a pump (D) to a second reservoir (C) which can be used to supply material that aids in maintaining steady state growth. For example, the second reservoir might contain a base for controlling the pH of the fluid within the fermentor.

As shown in the figure, the fermentor has an outlet portion (F) which is used to remove material via pump (G) to waste container (R). This outlet should have a tube that extends down into the fermentor and which is positioned so as to maintain the fluid level at a defined height. For example, the end of the tube extending into the fermentor might stop at the point where the top of the fluid level should be and pump (G) operated at a velocity sufficient to prevent fluid from rising beyond this point. The fermentor also has a paddle (L) for mixing fluid inside and a second outlet port (J). The second outlet has a tube that extends into the fermentor and below the fluid level inside. It is connected by tubing to pump (K) and to inlet port (N) of tissue culture flask (M).

The tissue culture flask shown in FIG. 1 (M) has a monolayer of eukaryotic cells growing on its bottom inside surface. These are perfused by bacteria-containing fluid from the fermentor which is introduced via inlet port (N) and removed via outlet port (O). The inlet port (N) may extend a short distance into the tissue culture flask and should, preferably, be positioned so that its tip touches a side wall of the flask, thereby allowing fluid to run to the bottom of the flask without unduly disturbing cells. The outlet port (O) can be used to maintain the fluid level within the flask at a defined height in the same way that outlet port (F) is used to maintain a defined fluid level within the fermentor. As shown in the figure, the outlet port (O) is connected to a pump (P) that can be used for transporting perfusate from the tissue culture flask into waste container (Q).

As mentioned above, the apparatus employs components that are readily available to one of skill in the art. For example, fermentors for growing bacteria under steady state conditions are commercially available and choosing appropriate diameters for inlet and outlet ports is routine in the art. Methods for modifying plastic tissue culture flasks so that they have an inlet and outlet port have been previously described (see U.S. Pat. No. 5,565,353; or U.S. Pat. No. 5,693,537) and can be used to construct flasks suitable for the present apparatus. In general, it is a simple matter to puncture plastic flasks using heated syringe needles. For example, an inlet needle may be inserted such that the bevel of the needle is 5 to 6 mm above the tissue culture monolayer and in contact with the side wall of the flask to minimize turbulence of the flow. The outlet needle should be inserted such that the bevel of the needle is positioned at the top of the fluid level and determines the volume of fluid within the flask.

It will be appreciated that many variations can be made in the apparatus components or their relationship without altering the basic underlying concept of linking a continuous culture fermentor for growing bacteria at a steady state to a vessel containing eukaryotic cells that have been immobilized on a solid support. For example, instead of using a tissue culture flask, eukaryotic cells can be grown on a porous support (e.g., beads or membranes) which are then loaded in a column. Under these circumstances, the top of the column would form the inlet port and the bottom, the outlet port. It should also be possible to adapt other cell culture vehicles, e.g., roller bottles, for use in the device. The size of the various components is not critical to the invention and can be adapted to the needs of the operator and the volumes of cells desired.

The apparatus described above can be used in a number of methods that are also part of the invention. Each of these methods has, as an essential feature, the perfusion of immobilized eukaryotic cells by bacteria that have been grown under steady state conditions at a defined rate. After perfusion, the invasiveness of the bacteria can be determined by processing eukaryotic cells and quantifying the number of invaded bacteria.

This system can be adapted for a number of purposes. The first is to separate bacteria that attach to eukaryotic cells from those that do not. Thus, the system can be used as method for isolating the particular bacteria responsible for disease development so that they can be further studied or used for the making of antibodies. The system can also be readily adapted to an assay for determining whether a particular test compound blocks the attachment and lysis of eukaryotic cells by bacteria. This is accomplished by comparing lysis occurring in the presence of the test compound with that occurring in its absence.

Finally, the present system offers a way to determine how growth rate affects the ability of bacteria to interact with a eukaryotic host cell. By comparing the extent to which eukaryotic cells have been invaded under different conditions, a set of parameters can be arrived at that produce highly invasive bacteria. Bacteria optimized for attachment and invasion would be especially well suited for the making of antibodies that can be used diagnostically to determine the extent to which a test sample of bacteria is likely to be harmful and therapeutically to interfere with the interactions between bacteria and host.

EXAMPLES

The following example demonstrates that the conditions under which bacteria are grown can have a substantial affect on their ability to invade host cells.

A. Methods

Although harmless as a member of the normal human bacterial gut microflora, group B *streptococcus* (GBS) can be life threatening when vertically transmitted to a newborn from a vaginally or rectally colonized mother during birth (Baker, et al., "Group B *streptococcal* infections, in: *Infectious Diseases of the Fetus and Newborn Infant,* W. B. Saunders ed, Philadelphia, PP 742–811 (1990)). Human isolates of GBS are surrounded by capsular polysaccharides (CPS). These antigens are major virulence factors as they serve to protect GBS from host defense mechanisms.

Expression of several surface antigens of GBS, including CPS, has been shown to be regulated by the rate of cell growth (Paoletti, et al., *Infect. Immun.* 64:1120–1126 (1996); Ross, et al., *J Bacteriol.* 181:5389–5394 (1999)). Different growth rates were achieved using GBS grown in chemically defined medium in continuous culture. In continuous culture, bacteria achieve a steady state of growth by precise control of nutrients, pH and oxygen. In the present example, it is demonstrated that precise control of GBS growth, and thus CPS expression, has an impact on the ability of GBS to attach to and invade permissive eukaryotic cells.

Figure 2A:
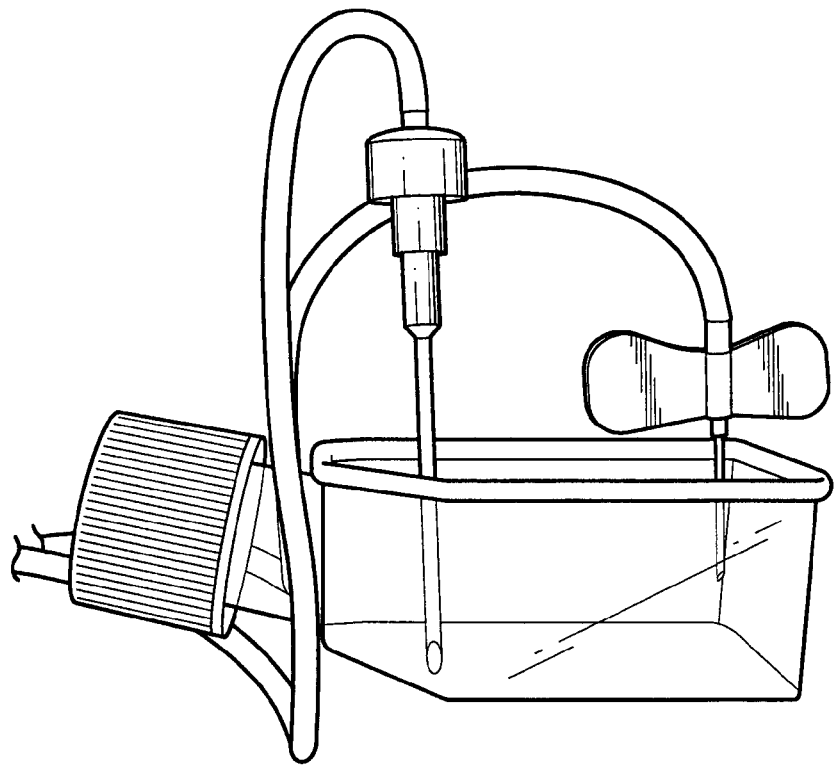
FIG. 2 (Panels A–B)
Figure 2B:
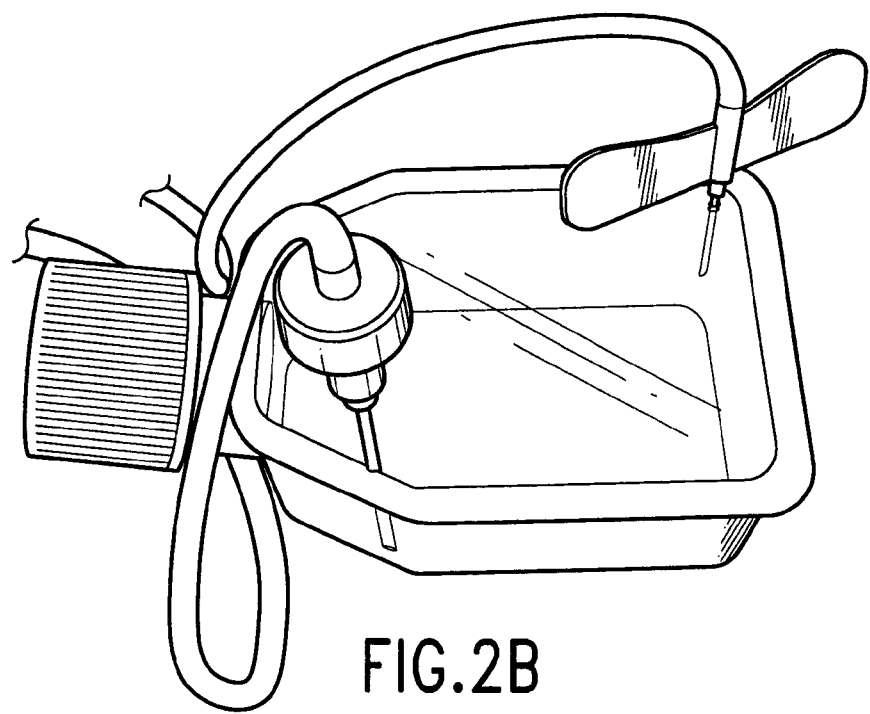

To test the above hypothesis, the in vitro attachment and invasion system shown in FIG. 1 was developed. This system combines the advantages of controlling bacterial growth using continuous culture methods with tissue culture. The cell culture flasks used in the system were modified (see FIG. 2) to allow bacteria from the chemostat fermentor to perfuse over an established monolayer of respiratory epithelial cells. Serotype III GBS strains M781, COH-1, and a transposon mutant of COH-1 (Rubens, et al., *Proc. Nat'l Acid. Sci. USA* 84:7208–7212 (1987)) that lacks CPS (strain COH1-13) were grown in continuous culture in a chemically defined medium at a fast ($t_d$=1.8 hours) and at a slow ($t_d$=11 hours) rate, conditions previously shown to influence type III CPS expression. The COH-1 strains have previously been shown to attach to and invade A549 respiratory epithelial cells using batch culture growth conditions and conventional attachment and invasion protocols (Rubens, et al., *Infect. Immun.* 60:5157–5163 (1992); Tamura, et al., *Infect. Immun.* 62:2450–2458 (1994)). Thus, these strains and tissue cell line serve as useful reagents to validate and evaluate the apparatus of FIG. 1 and associated methodologies.

B. Results

All GBS strains tested invaded A549 respiratory epithelial cells significantly better when grown at the fast, rather than slow, rate. Determining invasiveness based upon colony forming units (CFU) that invaded the confluent A549 cells in a 12.5 cm flask, it was found that cells grown at the fast rate ($t_d$=1.8 hr) produced more than three times the number of colonies compared to bacteria grown at the slow rate ($t_d$=11 hr). In these experiments, the pH of the bacteria during growth was maintained at 7.3 and the cultured eukaryotic cells were perfused at a temperature of 37° C. with rotary shaking. The results obtained confirm that growth rates can affect bacterial invasiveness and that a system combining a bacterial continuous growth vessel with a vessel for growing adherent eukaryotic cells can be used to study the interactions between bacteria and their hosts.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. An apparatus for culturing cells comprising:

(a) a fermentor containing bacterial cells growing under steady state conditions, wherein said fermentor comprises:
  (i) at east one inlet port for receiving fluid containing materials needed to maintain steady state bacterial growth;
  (ii) at least one outlet port through which medium containing bacteria can pass; and
(b) a culture vessel containing eukaryotic cells attached to a solid support, wherein said culture vessel comprises:
  (i) at least one inlet port which is connected to an outlet port of said fermentor;
  (ii) at least one outlet port for removing fluid from said culture vessel; and
(c) means for moving fluid comprising the bacteria from an outlet port of said fermentor to a connected inlet port of said culture vessel.

2. The apparatus of claim 1, further comprising:
(d) means for removing fluid from an outlet port of said culture vessel.

3. The apparatus of claim 2, wherein said fermentor further comprises:
(e) a second outlet port for removing fluid from said fermentor, wherein said second outlet port is not connected to said culture vessel; and
(f) means for moving fluid out of said fermentor nd through said second outlet port.

4. The apparatus of claim 3, further comprising:
(g) a reservoir of nutrient medium for growing bacteria, wherein said reservoir is connected to an inlet port of said fermentor; and
(h) means for moving said nutrient medium from said reservoir of nutrient medium to the inlet port of said fermentor recited in (g).

5. The apparatus of claim 4, wherein said fermentor further comprises a second inlet port.

6. The apparatus of claim 5, further comprising:
(i) a second reservoir containing material for maintaining the steady state growth of bacteria, wherein said second reservoir is connected to said second inlet port of said fermentor; and
(j) means for moving fluid from said second reservoir to said second inlet port.

7. The apparatus of any one of claims 1–6, wherein said culture vessel is a tissue culture flask, tissue culture dish or multiwell plate.

8. The apparatus of claim 1, wherein said means recited in (c) is a pump.

9. The apparatus of claim 2, wherein said means recited in (c) is a pump.

10. The apparatus of claim 2, wherein each of the means recited in (c) and (d) is a pump.

11. The apparatus of claim 3, wherein each of the means recited in (c) and (f) is a pump.

12. The apparatus of claim 3, wherein each of the means recited in (c), (d) and (f) is a pump.

13. The apparatus of claim 4, wherein each of the means recited in (c), (f) and (h) is a pump.

14. The apparatus of claim 4, wherein each of the means recited in (c), (d), (f) and (h) is a pump.

15. The apparatus of claim 5, wherein each of the means recited in (c), (f), and (h) is a pump.

16. The apparatus of claim 5, wherein each of the means recited in (c), (d), (f), and (h) is a pump.

17. The apparatus of claim 6, wherein each of the means recited in (c), (f), (h) and (j) is a pump.

18. The apparatus of claim 6, wherein each of the means recited in (c), (d), (f), (h) and (j) is a pump.

19. The apparatus of any one of claims 1–6 or any one of claims 8–18, wherein said fermentor further comprises a device for mixing fluid within said fermentor.

20. The apparatus of claim 19, wherein said device for mixing fluid within said fermentor is a stir motor driven paddle.

21. The apparatus of claim 19, wherein said culture vessel is a tissue culture flask, a tissue culture dish or a multiwell plate.

* * * * *